United States Patent [19]
Spanswick

[11] Patent Number: 5,905,262
[45] Date of Patent: May 18, 1999

[54] RADIATION MEASURING APPARATUS

[76] Inventor: Keith Albert Spanswick, 6 Kings Ct., Commerce Square, The Lace Market, Nottingham, NG1 1HS, United Kingdom

[21] Appl. No.: 08/806,822

[22] Filed: Feb. 26, 1997

[30] Foreign Application Priority Data

Feb. 27, 1996 [GB] United Kingdom .................... 9604140

[51] Int. Cl.$^6$ ........................................................ G01T 1/20
[52] U.S. Cl. .................. 250/368; 250/361 R; 250/483.1
[58] Field of Search ............................... 250/361 R, 367, 250/368, 369, 483.1

[56] References Cited

U.S. PATENT DOCUMENTS

| | | |
|---|---|---|
| 3,668,528 | 6/1972 | Hutchinson et al. . |
| 3,693,089 | 9/1972 | Hutchinson et al. . |
| 3,748,583 | 7/1973 | Anderson et al. . |
| 3,805,915 | 4/1974 | Payne . |
| 3,851,123 | 11/1974 | Lipinski et al. . |
| 3,925,977 | 12/1975 | Maezawa . |
| 4,595,014 | 6/1986 | Barrett et al. ............................ 128/654 |
| 4,605,859 | 8/1986 | Dilanni et al. . |
| 4,608,655 | 8/1986 | Wolf et al. . |
| 4,631,411 | 12/1986 | Noback . |
| 4,788,436 | 11/1988 | Koechner ............................ 250/268 X |
| 4,818,884 | 4/1989 | Saubolle . |
| 4,857,739 | 8/1989 | Phelps . |
| 4,996,429 | 2/1991 | Günter ................. 250/336.1 |
| 5,006,714 | 4/1991 | Attix ....................... 250/368 |
| 5,483,958 | 1/1996 | Merberg et al. ................... 250/368 X |

FOREIGN PATENT DOCUMENTS

| | | |
|---|---|---|
| 54-107791 | 8/1979 | Japan . |
| 57-50672 | 3/1982 | Japan ................... 250/368 |
| 2-19788 | 1/1990 | Japan . |
| 645732 | 10/1984 | Sweden . |

OTHER PUBLICATIONS

"Computer Interfacing Automatic–Dosimetry Systems (CID)", Dosimeter Corporation (Cincinnati, OH 1983).

"Dosimeter Corporation's Computer Interfacing Automatic Dosimeter (CID) System", *Radiation Protection Management*, 2/4:67–73 (Jul. 1985).

"Personal Digital Dosimeter, Model 885", Victoreen, Inc. (Cleveland, OH, 1989).

Street, et al., "Charge–Coupled Devices and Solid State Optical Sensors IV", *SPIE*, 2172:144–154 (Feb. 7–8, 1994).

Street, et al., "Amorphous Silicon Arrays Develop a Medical Image", *IEEE*, pp. 38–42 (Jul. 1993).

Tannas, "Evolution of Flat–Panel Displays", *Proceedings of the IEEE*, 82:4, pp. 499–509 (Apr. 1994).

Antonuk, et al., "Considerations for High Frame Rate Operation of Two–Dimensional a–Si:H Imaging Arrays", *Materials Research Society Symposium Proceedings*, 297:945–950 (1993).

Vidisco, Ltd., Sales Brochure for "A–500E Portable Video Based X–Ray Inspection System" (1994).

"Electronic Personal Dosimeter", Plessey Controls Ltd. (Dorset, UK, Oct. 1988).

(List continued on next page.)

*Primary Examiner*—Edward J. Glick
*Attorney, Agent, or Firm*—Fitch, Even, Tabin & Flannery

[57] ABSTRACT

Radiation measuring apparatus includes a sensor assembly (10) including a sensor (16) which includes a scintillating body (30, 30') that absorbs radiation to be sensed and converts it to light. A measuring device (38) measures the intensity of the light emitted by the scintillating body and thereby indicates the amount of radiation to which the body (30) has been exposed. The sensor assembly may also include an optical fiber (12) by which the light emitted by the scintillating body is conducted to the measuring device (38). A plug (14) located on an end of the optical fiber remote from the sensor (16) is adapted to be detachably inserted in a connecting socket (40) of the measuring device (38). In this way the sensor assembly (10) is readily exchangeable for a new assembly.

21 Claims, 6 Drawing Sheets

OTHER PUBLICATIONS

"Stephen Digital Dosimetry System", Bicron Corporation (Newbury, OH, 1989).

"Rad–80 Pocket Dosimeter", Alnor Nuclear Corporation (Pittsburgh, PA), (No date).

"Testing of the Alnor RAD–80R Against Specifications in Draft ANSI Standard N42.17A", Battelle, Pacific Northwest Laboratories (Richland, WA) (1987).

"Alarm Pocket Dosimeter (APD)", Panasonic, Matsushita Electric Trading Co., Ltd. Osaka, Japan, 1986).

"Digital Survey & Dosimeter PSD–6021A", Nagase & Co., Ltd. (Tokyo, Japan).

"Mini–Chirper", Xetex Inc. (Sunnyvale, CA) (1987).

"IMP Dosimeter, Model 444A" Xetek, Inc. (Sunnyvale, CA) (1988).

"Pocket–sized geiger counter", *Encyclopedia of Electronic Circuits*, 2:514–515 (1988).

"Research News: Computerized Wristwatch Dosimeter", *HPS Newsletter*, p. 6 (1985).

"Inductive coil used to charge batteries and read out data from $170 dosimeter", *Electronics*, (Jan. 1977).

"Subminiature Digital Ratemeter and Dosimeter Using MOS Technology", *Health Physics*, 27/1 (1974).

RADIATION MEASURING APPARATUS

BACKGROUND OF THE INVENTION

This invention relates to radiation measuring apparatus and is especially concerned with measurement of X-ray radiation. More especially, the invention relates to the real-time measurement and display of relatively low intensity X-ray radiation using a sensor which is sufficiently small so as not to interfere with the measurement and image-forming process commonly used during radiological procedures. The invention may also be of use in the measurement of other forms of radiation.

In some circumstances the human (or animal) body can be exposed to X-ray radiation of relatively low intensity for a long period of time, for example, when used for guidance during surgical procedures. This relatively lengthy but low level of exposure has, in some cases, led to severe skin burns. Skin doses of 400R (4Gy) are not unusual when procedures such as RF cardiac ablation or intrahepatic shunt placement are being carried out. Severe latent skin reactions have been seen following such procedures.

As a result of the potential for excessive exposure to X-ray radiation, the Food and Drug Administration (FDA) of the United States recently (Sep. 30, 1994) issued a Public Health Advisory entitled "Avoidance of Serious X-Ray Induced Skin Injuries During Fluoroscopically Guided Procedures". This advisory recommended that information be recorded in the patient's medical record to permit estimating absorbed dose to the patient's skin. The purpose of the recommendation was, of course, to encourage identification of those areas of the skin which are irradiated at levels of absorbed dose that approach or exceed a threshold for injury. This FDA advisory was followed by a second FDA advisory (Sep. 15, 1995), "Recording Information in the Patient's Medical Record That Identifies the Potential for Serious X-Ray-Induced Skin Injuries Following Fluoroscoptically Guided Procedures", which clarified which patients should have the information recorded and what information should be recorded. Both of these FDA advisories are incorporated herein by reference.

While various proposals have been made for checking the exposure of radiation in real time, the dose monitors needed to perform such checking have not heretofore been available. Such dose monitors must be sufficiently small so as not to interfere with radiological images, and should also be readable and monitorable during the exposure procedure.

There is thus a need in the art for an improved radiation measuring apparatus which can be read in real time during radiological procedures, and which is sufficiently small so as not to interfere in an unacceptable way with the radiological images resulting from the radiological procedures.

The present invention advantageously addresses the above and other needs.

SUMMARY OF THE INVENTION

The present invention provides radiation measuring apparatus comprising a radiation sensor assembly coupled to a radiation monitoring device. The sensor assembly includes a radiation sensor, which sensor includes a scintillating body which converts absorbed radiation to light. The monitoring device comprises a means for measuring the intensity of the light emitted by the scintillating body and a means for displaying or indicating the amount of radiation to which the body has been exposed.

The light emitted by the scintillating body that forms part of the sensor assembly typically has a wavelength in the visible spectrum. It is to be understood, however, that scintillating bodies that emit light or radiation that does not lie in the visible spectrum may also be used with the invention. The key requirement is that the radiation monitoring device be equipped to detect whatever radiation is emitted by the scintillating body.

Preferably, the sensor assembly is detachably connected to the monitoring device. A preferred sensor assembly includes flexible optical fiber means by which light emitted by the scintillating body is conducted to the monitoring device. Conveniently, one end portion of the optical fiber means is terminated by connector means, for example, a plug connector, by which the optical fiber means may be detachably connected to the monitoring device.

In accordance with one aspect of the invention, the scintillating body is shrouded by a reflective material which reflects light impinging thereon and directs it towards the optical fiber means for transmission to the monitoring device.

In accordance with another aspect of the invention, the sensor and adjacent portions of the sensor assembly are shrouded by an opaque cover, thereby preventing light other than that emitted by the sensor body from reaching the optical fiber means. Such cover is preferably opaque to light having a wave length which can be transmitted by the optical fiber means and which can be detected by the monitoring device. However, such cover is essentially transparent, or at least radio translucent, to X-ray radiation, thereby assuring that only the tiny active element of the scintillating body is visible on the resulting X-ray image.

In one preferred embodiment of the invention, the sensor body is shrouded within a pad assembly of the sensor assembly. Such pad assembly is transparent to the radiation to be measured. Advantageously, the pad assembly is adapted to facilitate its mounting on a surface, e.g., the skin surface, that lies within an image plane or exposure place where the radiation measurement is being made. Conveniently, the pad assembly is adapted to be secured to the surface by an adhesive. Suitably, the pad assembly comprises a flexible, resilient material which will be such as to provide some mechanical insulation between the surface to which the pad assembly is attached and the sensor body carried within the pad assembly.

The pad assembly is preferably disc shaped having a diameter less than about 50 mm. Where the sensor assembly is used as a radiation skin dose monitor—a common use for the invention—it may have a diameter of only about 35 mm, thereby allowing it to be positioned within the image plane, e.g., within a corner of the image plane. Because most of the pad assembly, with the exception of the small scintillating body used therein, is transparent or at least radio translucent with respect to X-ray radiation, only the small scintillating body is visible on the resulting x-ray image that is formed.

In accordance with one aspect of the invention, each sensor assembly is guaranteed for a minimum of 10 uses. However, under normal working conditions, the sensor is typically reusable 30 to 40 times. Deterioration of the sensor assembly does not generally occur due to deterioration of the scintillating element used therein. Rather, sensor breakdown, if it occurs, is typically in the nature of physical damage, e.g., either the optic fiber cable becomes severely kinked, or light leaks develop that allow light leakage into the coupling of the optical fiber with the monitoring device.

The monitoring device used with the invention functions as light measuring means. Typically, the monitoring device measures the amount of impinging light and is so constructed and arranged so as to indicate the total amount of radiation to which the sensor body has been exposed and/or so as to indicate the instantaneous rate of exposure to radiation.

Any suitable material may be used to construct the scintillating body of the sensor. Typically, this material is chosen according to the use to which the sensor is to be put. Where the apparatus is to be used for monitoring the dosage of X-ray radiation to which the skin is exposed, for example, one suitable material for construction of the body is a thallium doped caesium iodide crystalline material. Another suitable material for the scintillator is zinc cadmium sulphate-Ag.

For greatest sensitivity, it is desirable that the scintillator body be of sufficient size to absorb all the X-ray radiation impinging upon it, but also must not significantly attenuate the limited light before it is transmitted into the optical fiber means. With the aforementioned doped caesium iodide material, the body is preferably less than 0.3 mm thick, suitable between about 0.1 mm and 0.2 mm in thickness. The volume of the body is preferably less than about 0.3 cubic mm.

It is to be understood that the invention is not limited to the radiation measuring apparatus that includes both the sensor assembly and the monitoring device, as described above, but also is directed to a sensor assembly suitable for use in making radiation measurements. Such sensor assembly may take many forms, but preferably includes a flexible optical fiber means having a plug connector, or equivalent, at one end portion and a sensor at the opposite end portion. The sensor includes a scintillating body secured to an end face of the optical fiber means and formed of a material which emits visible light when the body is exposed to radiation. Preferably, the scintillating body is shrouded by light reflective material which tends to direct light emitted by the body, and/or impinging on the reflective material, towards the optical fiber means. Suitably, the sensor and adjacent end portion of the optical fiber means are also shrouded by an opaque material to prevent light entering the fiber means other than the light emitted from the body of the sensor. The sensor body may further be shrouded by a pad assembly to facilitate attachment of the sensor to a surface.

The present invention may also be considered to comprise a kit of parts that includes a sensor assembly in accordance with the invention, a plurality of disposable means for attaching the sensor to a surface, and a number of recording means for recording data, where the number of recording means corresponds to the number of attaching means. Conveniently, the recording means comprise a record sheet (on which data may be entered) having one attaching means temporarily secured thereto.

BRIEF DESCRIPTION OF THE DRAWINGS

The above and other aspects, features, and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
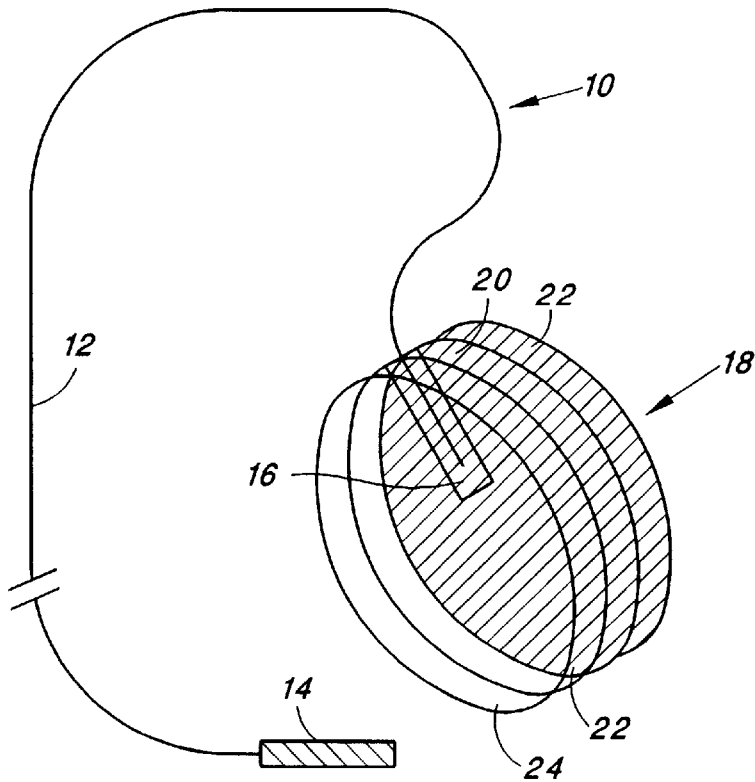
FIG. 1 is a perspective view of a sensor assembly embodying the invention.
Figure 3:
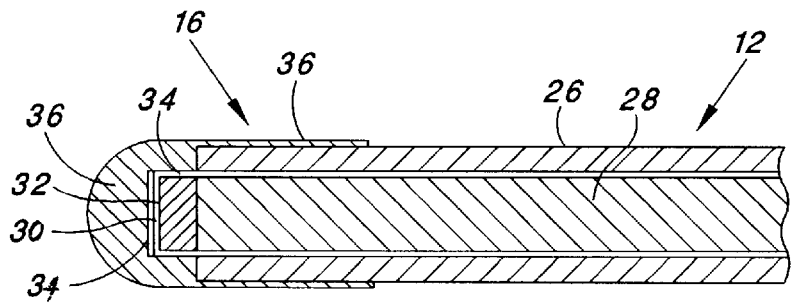
FIG. 3 is a sectional view showing one embodiment of a sensor carrying an end portion of an optical fiber in accordance with the invention.
Figure 2:
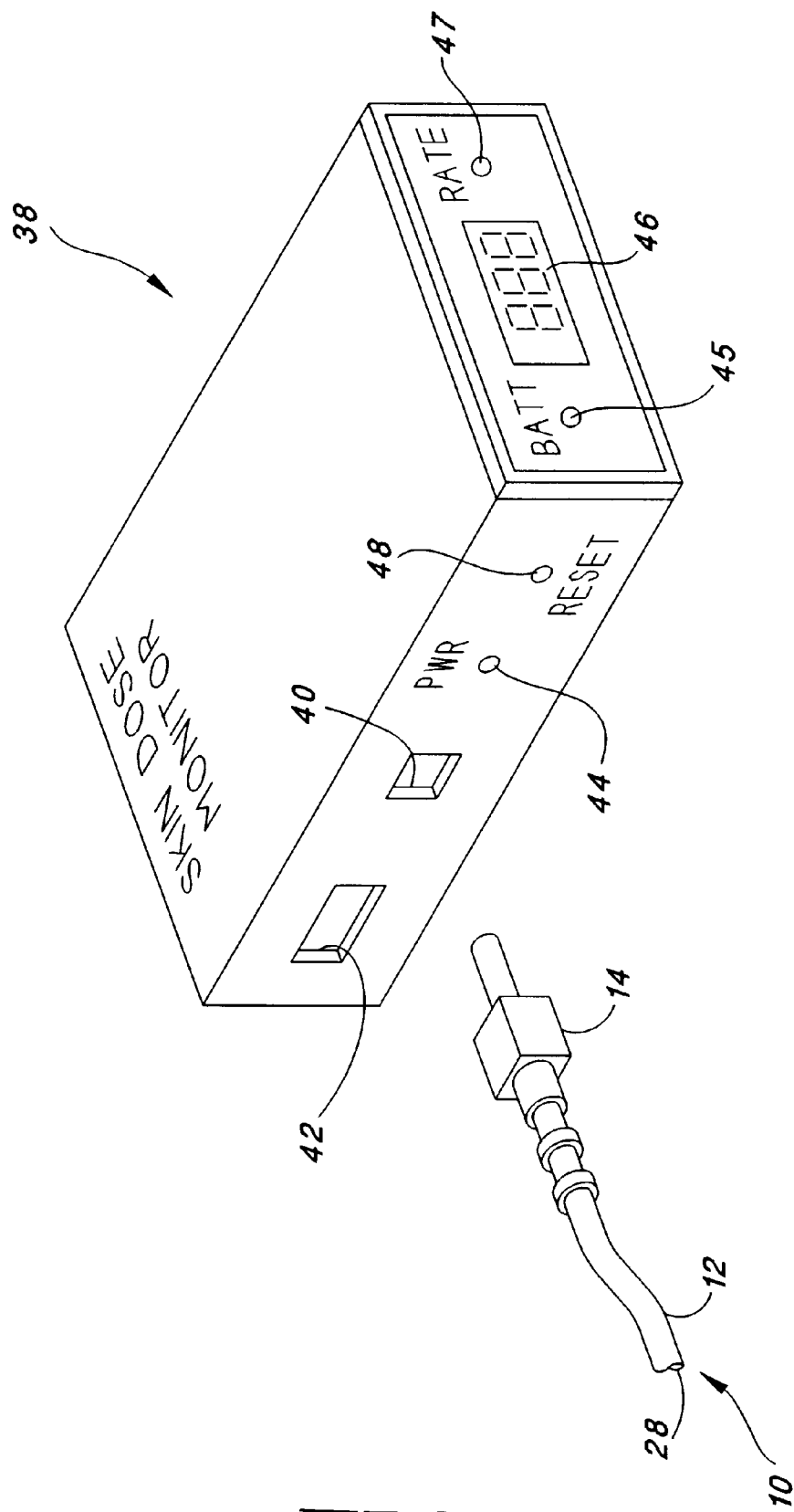
FIG. 2 is a perspective view of a monitoring device made in accordance with the invention.

An illustrative apparatus or system of the invention is illustrated in FIGS. 1–3. Such apparatus is suitable for use in monitoring the dose of X-ray radiation to which a region of skin of the human body is exposed. Such apparatus comprises a sensor assembly 10 embodying the invention, the assembly 10 including a sensor which includes a scintillating body 30 that absorbs X-ray radiation and converts it to visible light. The apparatus or system further includes measuring means 38 (FIG. 2) for measuring the intensity of the light emitted by the scintillating body 30 and indicating or displaying the amount of radiation to which the scintillating body 30 has been exposed.

Referring to FIGS. 1 and 3, it is seen that the sensor assembly 10 embodying the invention comprises an optical fiber 12 carrying a male plug connector 14 at one end, e.g., a proximal end of the fiber 12, and a sensor 16 at the opposite end, e.g., a distal end of the fiber 12.

The sensor 16 is shrouded by a pad assembly 18. The pad assembly 18 is transparent (or at least translucent) to the X-ray radiation which is to be measured by the sensor assembly 10 and is adapted to facilitate mounting of the pad assembly 18 on a suitable surface, e.g., on the skin surface of a patient. The pad assembly 18 conveniently is of a disc shape having a diameter of about 35 mm, and is made up of a number of layers of material. For example, a support layer 20 (which may be of a fairly rigid material) provides a substrate to which the sensor may be secured to provide some protective support. Two protective layers 22 sandwich the support layer 20 and the sensor 16. The layers 22 each comprise a flexible resilient material, for example, a flexible resilient plastic foam material which provides some protection against mechanical shock which could otherwise damage the sensor. An attachment layer 24 may also be provided on one or both outer surfaces of the layers 22. The attachment layer 24 may be, for example, a layer of adhesive (which may, if desired, be covered with a protective layer which can be peeled off to expose the adhesive for attachment of the pad assembly to a surface) or may be a surface layer of one of either of the layers 22 suitable to accept a subsequently applied adhesive layer or to connect with some other means for attaching the pad assembly to a surface.

The optical fiber 12 preferably comprises a plastic fiber optic core 28 sheathed in an opaque protective covering material 26. Such optical fiber 12 is of known construction and is commercially available from numerous vendors.

In one embodiment, the sensor 16 is disposed at one end of the optical fiber 12 (see FIG. 3) and comprises a scintillating body 30 which absorbs X-ray radiation falling on it and converts such absorbed radiation to visible light. For monitoring the dose of radiation to which an area of skin has been exposed, the scintillating body 30 is conveniently made of a thallium doped caesium iodide crystalline material (CsI(T)). Alternatively, the body 30 may be made from Zinc Cadmium Sulphate-Ag.

In the sensor assembly illustrated in FIG. 3, the core 28 of the optical fiber 12 has a diameter of 1 mm, and the scintillating body 30 is of a corresponding size having dimensions of roughly 0.25 mm thick by 1 mm diameter, providing a volume of about 0.2 mm$^3$. However, the precise size and volume of the scintillating body 30 should be selected dependent upon the material from which it is to be made, the volume of material necessary to absorb all of the X-ray radiation for the wavelength under investigation which falls on the body, and having a material thickness that will not unduly attenuate the light emitted by the scintillating material sufficiently to distort the readings provided by the sensor. Preferably, the scintillating body 30 is shaped and dimensioned to convert as much as possible of the radiation entering it to visible light and to ensure that as much as possible of the emitted light enters the fiber optic core 28 for transmission to the measuring device 38. An alternative embodiment for achieving this goal is discussed below in connection with FIGS. 4 and 5.

The scintillating body 30 is secured to the end face of the fiber optic core 28 using a suitable adhesive compound having a refractive index compatible with both the core 28 and body 30 (usually intermediate that of the core 28 and body 30) so that the adhesive does not interfere with the passage of light from the body into the fiber optic core 28. Suitable UV curable adhesives are commercially available for the purpose of bonding lenses or the like to end faces of optical fibers.

In operation, light falling on a flat end face 32 of a fiber optic core 28 will be accepted for transmission by the core 28 provided that the direction of incidence of the light on the face falls within a cone having as its axis the central axis of the fiber optic core 28. The angle of such cone has a particular angle referred to as the acceptance angle. It is therefore important to ensure that as much light as possible emitted by the body 30 is directed within this acceptance angle towards the end face of the core 28. To this end, therefore, the scintillating body 30 is shrouded by a reflective material 34 which reflects visible light of the emitted wavelength and tends to direct this visible light impinging on it towards the end face of the fiber optic core 28 for transmission along the fiber optic core 28. It has been found that white printing ink provides a suitable light reflective coating, but other reflective material may equally well be used, provided that it is transparent to the radiation to be measured.

The sensor 16 further includes a shroud or opaque cover 36, preferably coated on its inside surface with the reflective material 34, to prevent light other than that omitted by the scintillating body 30 from reaching the end face 32 of the fiber optic core 28.

Referring next to FIG. 2, the illustrative apparatus or system also includes a monitoring or measuring device 38. The device 38 performs the function of a skin dose monitor (SDM), and as such, measures the amount of light received through the optical fiber 12, resulting from light emitted by the scintillating body 30, which light is proportional to the amount of radiation absorbed by the scintillating body 30. Preferably, the device 38 is a small, relatively light weight, portable apparatus. Conveniently, the measuring device is powered by batteries (not shown), e.g., rechargeable batteries, and is a low voltage device. However, if desired, the measuring device could be powered from a main power source, e.g., a 110 or 220 VAC wall plug, with the optical fiber 12 providing full electrical isolation between the measuring device 38 and the sensor 16.

The measuring device 38 includes a plug socket 40 into which the plug connector 14 of the sensor assembly 10 is inserted to provide a connection by which the light traveling along the fiber optic core 28 can be introduced into the measuring device 38. The plug 14 and socket 40 are of known construction and are arranged so that the plug 14 may be readily removed from the socket 40 so that the sensor assembly 10 can be replaced by a similar sensor assembly whenever necessary.

The batteries used within the device 28 may be conventional batteries, e.g., AA batteries, which can be replaced when spent, or they may be rechargeable batteries, which may be recharged from a main power source through a wall plug connected to the measuring device 38 by a conventional power cord plugged into a socket 42. The measuring device 38 has an ON/OFF switch 44 which allows the batteries to be selectively connected to the measuring circuits within the device 38 (device turned ON) or disconnected from the measuring circuits (device turned OFF). A battery indicator light 45, which may be realized with, e.g., a light emitting diode (LED), turns ON whenever the device 38 is turned ON by the power switch 44. A low battery condition (i.e., the batteries need replacing and/or recharging) may be indicated by a blinking or flashing light 45, or by a change in color of the LED 45, or through some other suitable low-battery indicating means.

The measuring device 38 includes electronic circuitry, explained below in connection with FIG. 6, which provides a measure of the total radiation to which the scintillating body 30 of the sensor 16 has been exposed. This measure of radiation is displayed on a liquid crystal display (LCD) 46 of the measuring device 38. A reset button 48 provides a means of resetting the display to zero when a new measurement is to be made.

The measuring device 38 may also include a light emitting diode 47 which flashes at a rate which indicates the rate at which radiation is being received. Alternatively, rather than have the device 38 display the total radiation to which the scintillating body 30 has been exposed, the display 46 may be configured to display in numerical terms the rate of exposure to radiation.

The electronic circuitry within the measuring device 38 records the light emitted by the sensor body 30 and displays the result on the liquid crystal display 46. Such circuitry may take many forms, as is known in the art. One such form is explained more fully below in conjunction with FIG. 6. Such circuitry typically includes a Silicon PIN photodiode sensitive to the wavelength of the light emitted by the crystalline scintillating body 30.

Advantageously, the measuring device 38 may be provided with a carrier (not shown) in which the measuring device 38 can be removably mounted. The carrier may be arranged to be suspended from any suitable point, for example, a bed frame.

The sensor 16 is arranged to give uniform excitation of the scintillation crystal body 30 irrespective of the angle at which the radiation falls on the crystal body 30. Because the sensor can measure the absorbed dose directly at the skin surface when the sensor is mounted by the pad assembly on a skin surface, this allows inclusion of back scattered radiation, which back scattered radiation can contribute up to 30% of the total skin dose.

Only the small scintillating body 30 is visible on a radiograph or flouromonitor or other image. This is because the optical fiber 12 is almost completely transparent to X-ray radiation. The optical fiber 12 also provides electrical isolation between the patient's skin and the measuring device 38.

The illustrative apparatus measures X-ray radiation in an energy range of 40–150 kVp and has a sensitivity of 1 nlm/mR/sec. The system accuracy is better than ±5% at 70 kVp.

Because of the small size of the scintillating body 30, and the transparency to X-ray radiation of the optical fiber 12, the illustrative sensor assembly does not interfere significantly with radiological images. Furthermore, the illustrative apparatus measures and displays the radiation dose in real-time. Thus, if the display indicates that the skin dose is approaching damage threshold levels, corrective action can be taken—for example a change in X-ray beam direction or a minimization of the use of further radiation. An alarm circuit may be incorporated into the measuring device 38 so that as a preset limit of radiation is approached, an alarm is triggered (e.g., an audio and/or visual alarm) which alerts all parties concerned that corrective action is needed.

It is noted that while the pad assembly 18 may conveniently be affixed to the patients's skin, it may also be applied to other surfaces adjacent the skin, for example, the gown of a patient, or a surface of the X-ray equipment, for example, the couch. Pad location is dependent on the particular procedure which is being undertaken. If it is known, for example, where the center of the radiation will be located on the patient's skin, then the pad 18 should be placed at, or close to, that position.

It is further noted that while the illustrative apparatus is intended to be used to monitor the radiation dosage to which skin is exposed, a generally similar type of apparatus may be used to monitor radiation in other circumstances. However, different sensors may be required depending upon the radiation to be monitored and the situation. The illustrative sensor is particularly designed to record X-ray radiation, but similar apparatus may be used to measure dosage of other types of radiation, for example, other types of radiation received in radiation therapy. In a preferred apparatus, a sensor assembly comprising a scintillator body responsive to the radiation of the wavelength to be measured is connected to measuring means, e.g., the measuring device 38, by an optical fiber 12. The apparatus will also need to ensure that as much as possible of the emitted light is transmitted by the optical fiber to the measuring means and to that end will use the various features discussed above, where appropriate.

The illustrative apparatus is initially calibrated against a radiation dose meter and may be supplied with gain setting controls which will allow user selection of calibration when used with an appropriate selector switch.

Figure 7:
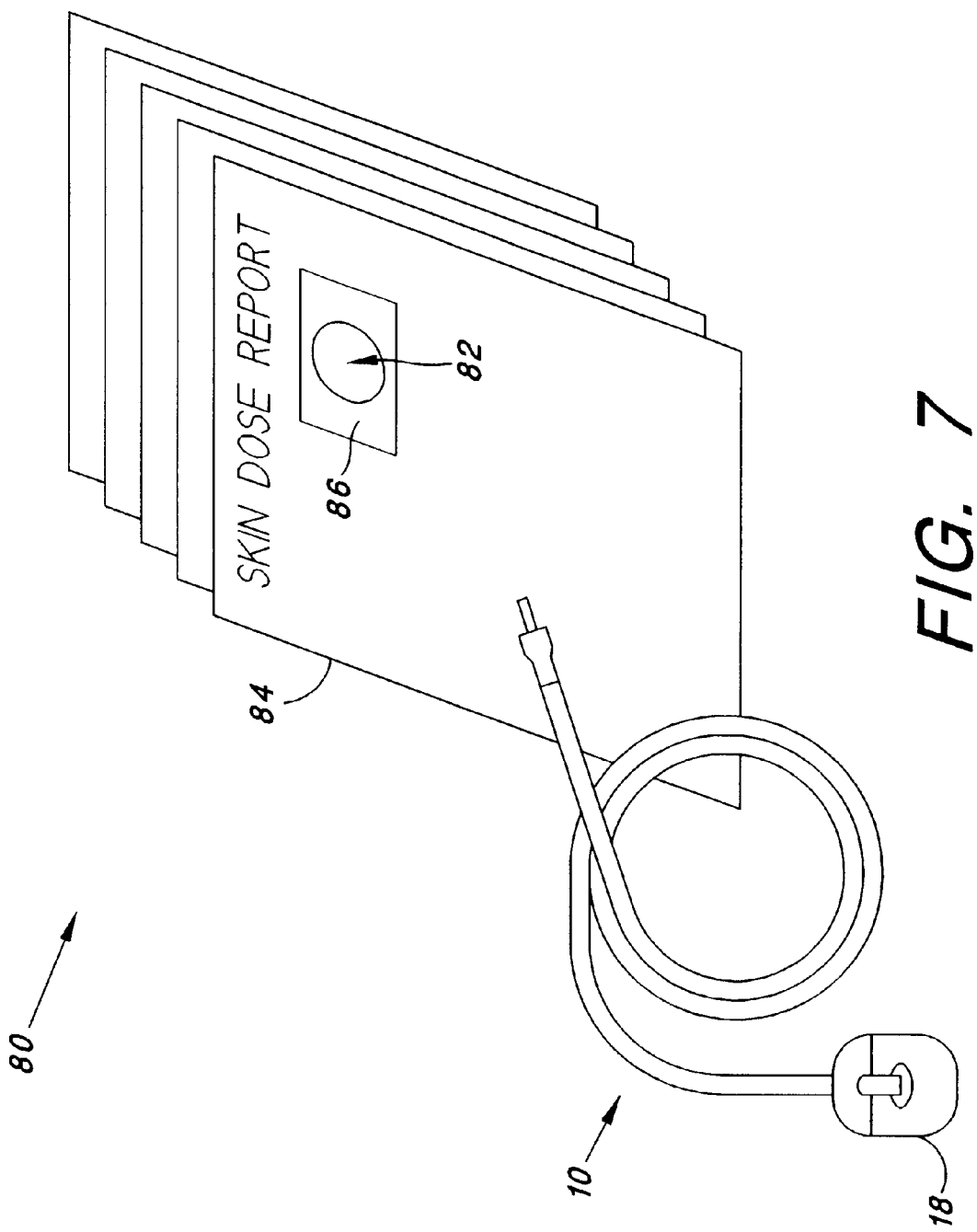
FIG. 7 illustrates a kit of parts in accordance with the invention that includes a sensor assembly, a plurality of disposable means for attaching the sensor to a surface, and a number of recording sheets.

Turning momentarily to FIG. 7, the invention also is directed to a kit of parts 80 comprising the illustrative sensor assembly 10 described above and a plurality of disposable means 82 for attaching the pad assembly 18 to a surface. The kit of parts 80 also includes a number of recording means 84, e.g., charts, provided by record cards or report sheets, corresponding in number to the number of disposable attaching means 82.

Within such a kit 80, the record cards 84 each include instructions for use of the sensor assembly including sterilization procedures, assistance for site identification, instructions for fixing the sensor of the sensor assembly and removal of the sensor, dose recording and disposal. These instructions conveniently may appear on one side of the report card and on the other side will appear the details relating to the patient being examined, the type of examination and other material required, and a region for recording the skin dose radiation measurement. The record cards may also include diagrams of a human body on which the site of radiation exposure may be marked.

Any suitable disposable attachment means may be used. However, the illustrative kit of parts comprises a sealed plastic bag 86 secured to the report sheet 84, wherein the bag 86 is adapted to accommodate the attachment means 82. The attachment means 82 in each sealed bag 86 preferably consists of two items, either of which may be used independently to mount the sensor 16 of the sensor assembly using the pad assembly 18. The first of these items is an adhesive disc which is sandwiched between two layers of protective material. One of the layers of protective material may be peeled off the adhesive disc (which is of the same diameter as the pad assembly) and the exposed adhesive disc applied to a surface of the pad assembly; the other protective layer may then be pealed off the adhesive layer which can be used to attach the pad assembly to the patient's skin (or indeed to any other surface). The other item of the attachment means which can be used instead of the adhesive disc comprises a hook and loop material fastener disc, the material being supplied under the Trade Name "Velcro", which has a pressure sensitive adhesive layer on one face of the Velcro material, the adhesive layer being protected by a release paper cover. In use, the release paper cover is peeled from the adhesive layer which is used to affix the Velcro material to a surface, for example, of a couch of X-ray apparatus at a desired position. The pad assembly of the sensor assembly may then be placed on the exposed Velcro material which will secure the pad assembly in place. In both cases the pad assembly can be readily peeled from the surface to which it has been attached. The used attachment means (namely the adhesive disc on the Velcro disc) should be removed from the surface to which it has been attached and disposed of as medical waste.

In use of the illustrative apparatus, a radiation count accumulates throughout the X-ray examination provided that the reset button is not operated. On completion of the examination, the measuring device 38 should be switched off by operating the power switch 44. Once turned off, the sensor can then be removed without the dose reading being lost, i.e., the dose reading remains displayed by the liquid crystal display until the reset button 48 is operated. Before use, the reset button 48 should always be operated to return the display to zero.

The kit of parts 80 contemplated by the invention typically includes one sensor assembly 10 and ten report sheets (each with an attachment means secured thereto as discussed above). The kit may be packaged in a sealed plastic bag which is opened when the sensor assembly is to be used. The illustrative sensor assembly is designed to be used up to ten times and a record sheet is provided for each of these ten uses. When these ten uses of the sensor assembly have taken place, the sensor assembly 10 may be unplugged from the measuring device 38 and disposed of as medical waste and exchanged for a new sensor assembly 10, which may then be removed from the bag of a further kit of parts and plugged into the socket 40 of the measuring device 38 as discussed above. The sensor assembly 10 that is included in a kit-of-parts should always have an indicated design life (number of uses) and a corresponding number of record cards (with combined attachment means) that corresponds with the design life of the assembly 10.

Figure 4:
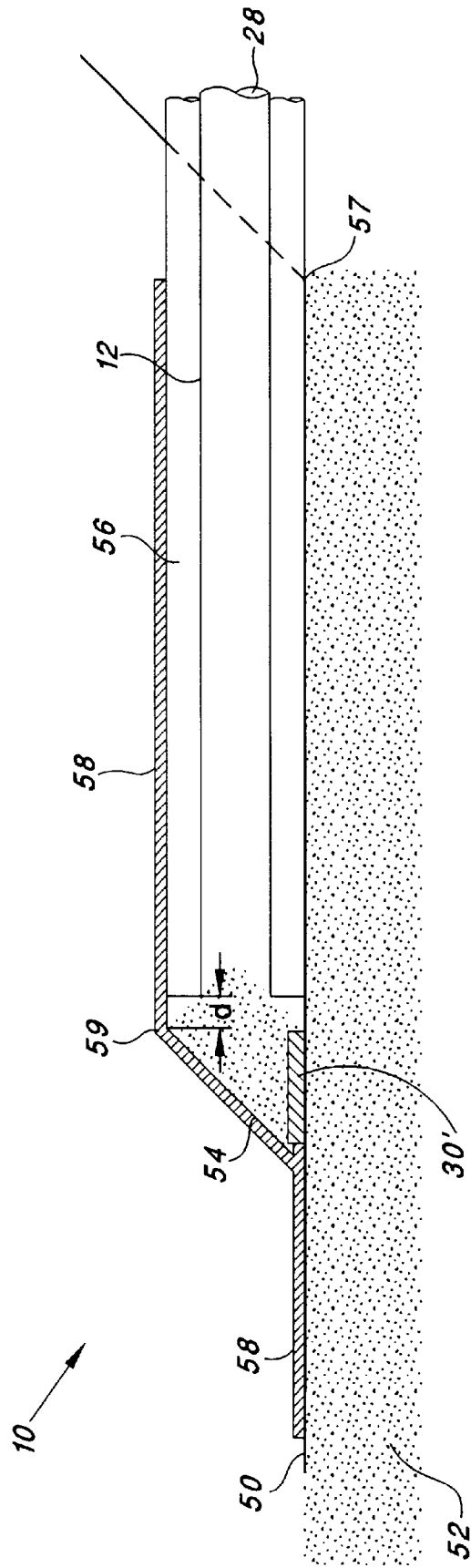
FIG. 4 is a sectional view of another embodiment of a sensor carrying an end portion of optical fiber in accordance with the invention.
Figure 5:
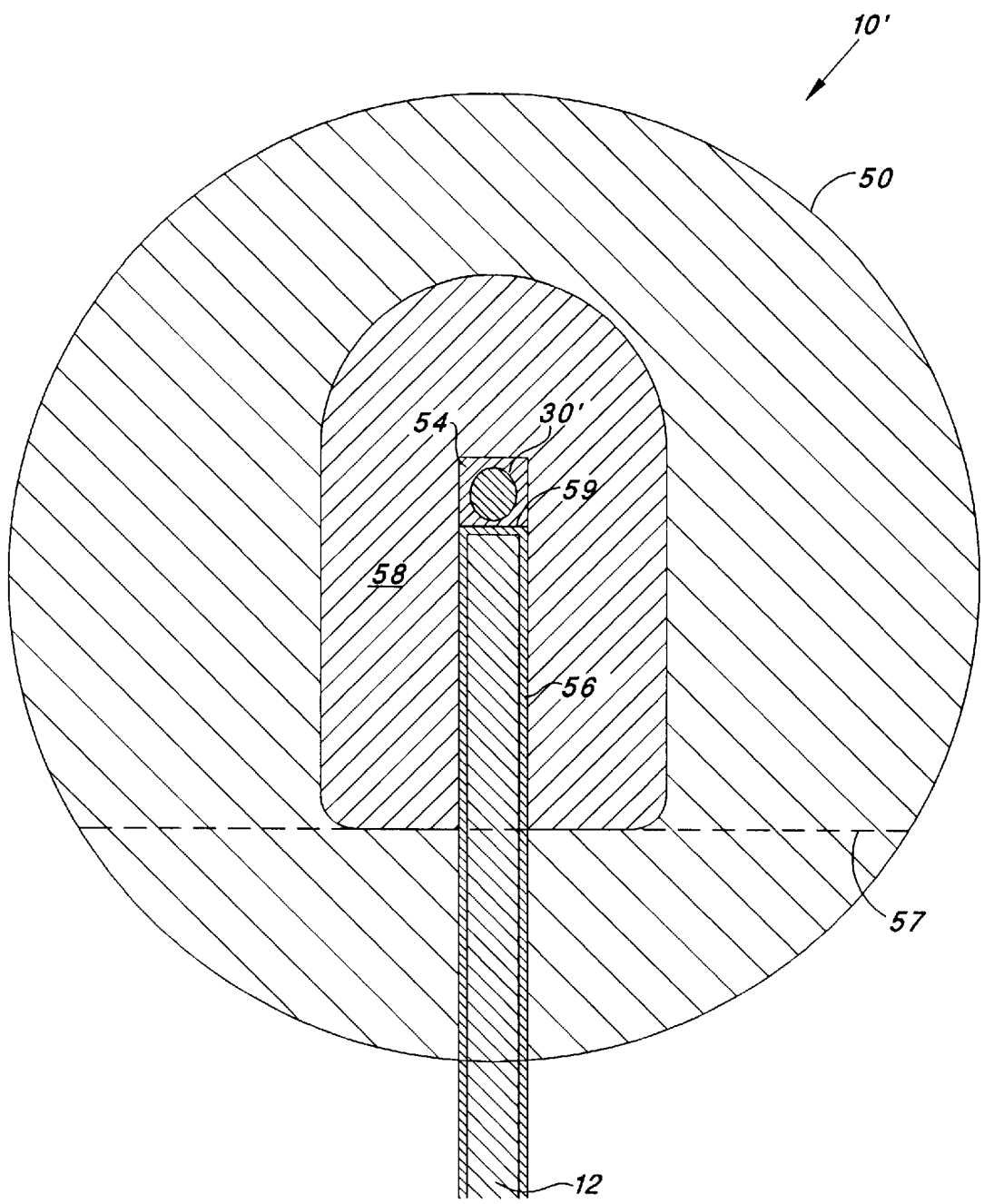
FIG. 5 is a top view of the sensor embodiment of FIG. 4.

Referring next to FIGS. 4 and 5, an alternative embodiment of a sensor assembly 10 is illustrated. FIG. 4 represents a side view of such assembly, and FIG. 5 shows a top view of the assembly. As seen in these figures, a scintillator 30', or scintillating crystal, is mounted on a sensor base disc 50. The base disc 50 is adapted to lie flat on a surface where a radiation measurement is to be made, e.g., on the surface of a patient's skin 52. The scintillator 30' is mounted on the base disc 50 so as to effectively lie in the same plane as the surface of the skin, thereby allowing the scintillator 30' to absorb a maximum amount of radiation.

The arrangement and geometry of the scintillator 30' is important to the present invention. Scintillators are normally selected to absorb the maximum amount of X-ray photons and convert these into visible light. The light is then sensed on the opposite face of the scintillator crystal to which the radiation enters. However, two techniques used by the applicant allow an energy response to be achieved that is similar to that in human tissue. First, a very thin crystal is used, whereby only a small proportion of the highly penetrating, high-energy, X-rays are absorbed. Second, by sensing the reflected image off of the X-ray entry face, rather than from the opposite face, the non-penetrating, low energy X-rays make a much greater contribution to the measured light output. These two techniques advantageously provide an energy response that is similar to that achieved in human tissue.

The scintillator crystal 30' is made from powdered particles reconstituted into a thin flat disc which is fixed parallel to the patient's skin 52 to best model skin absorption geometry. The crystal material is selected to emit red light which matches the point of maximum efficiency on the detector photo diode response curve. A preferred type of crystal material is zinc cadmium sulphate-Ag (i.e., zinc cadmium sulphate doped with silver).

A 45 degree mirrored surface 54 directs light from the scintillating crystal 30' to the light transmitting core 28 of the optical fiber 12. The optical fiber 12 is encased within a polypropylene sheath 56. This sheath is not easily fully bonded to other structures with adhesives. Hence, a molding layer 58 covers the end of the optical fiber 12, including its sheath 56, that overlays the base disc 50, as well as the mirrored surface 54 and surrounding areas. Also, a bend 57 is placed in the base disc 50, which bend serves as a cable restraint. That is, should the fiber 12 be pulled, the wall of the disc 50 digs into the fiber casing 56 and thus prevents the strain from being transferred to the fiber termination under the molding 58 in the region of the mirrored surface 54 and scintillator 30'.

In FIG. 5, it should be noted that part of the molding layer 58 is cut away to better show the manner in which the optical fiber 12 is laid along a top surface of the base disc 50, passing through a hole in the base disc 50 where the base disc is bent up at fold 57.

The mirrored surface 54 made be made in any suitable manner, but typically comprises an aluminized mirror coating that is evaporated onto the interior faces of the molding layer 58. Because the scintillator 30' is parallel to the patient's skin, the angular response of the sensor is improved. That is, the optical fiber 12 receives light that images the entrance face of the scintillator 30', rather than its exit face, thereby improving the energy response. Typically, the end of the optical fiber 12 closest to the scintillator 30' is positioned a distance "d" of approximately 0.5 mm from the upper bend 59 of the 45 degree mirror 54. Such positioning assures that most of the light emitted from the scintillator will be directed to and through the core 28 of the optical fiber 12.

Figure 6:
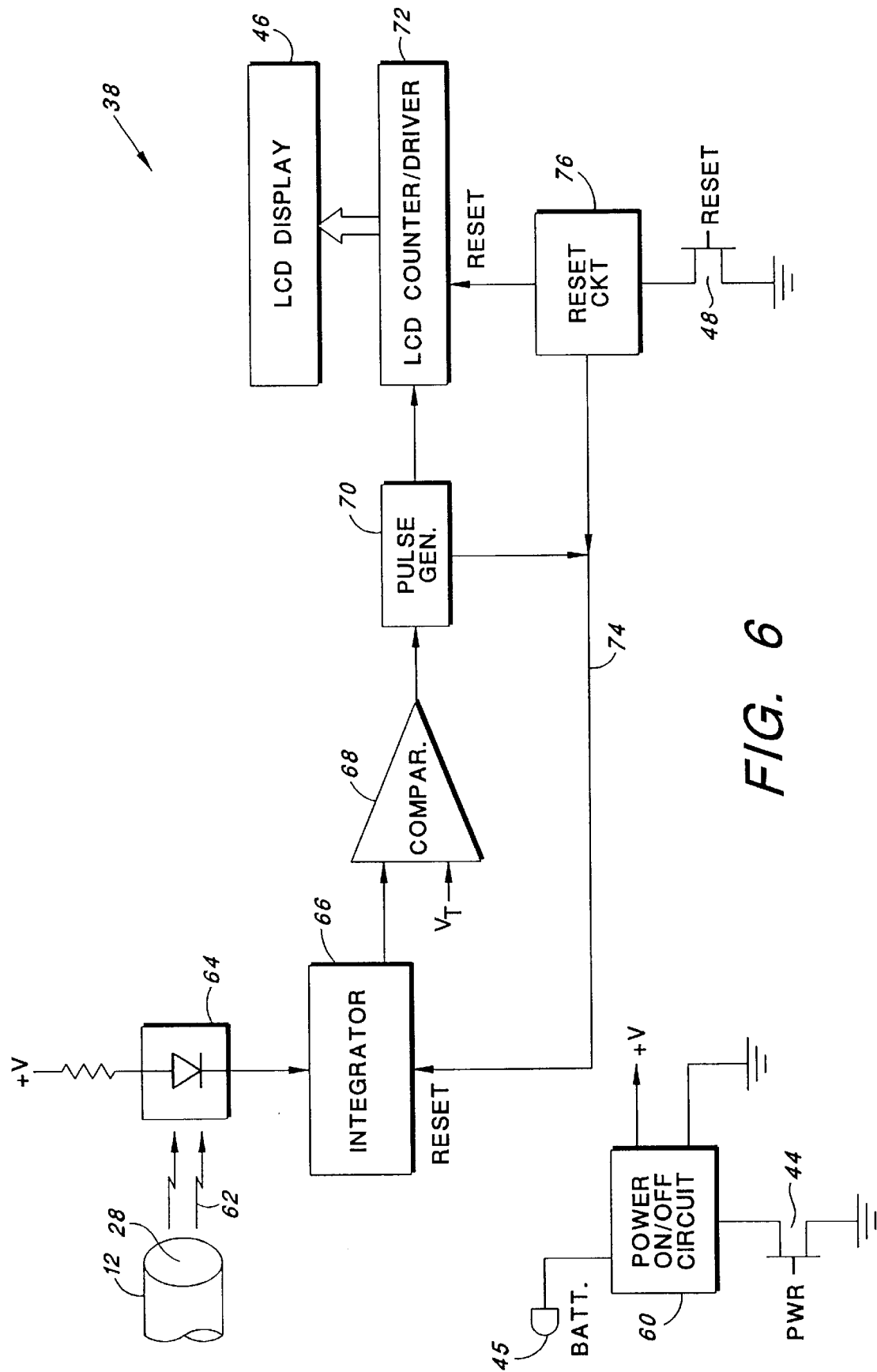
FIG. 6 is a functional block diagram of a representative monitoring device that may be used with the present invention.

Turning next to FIG. 6, a functional block diagram of the measuring device 38 is illustrated. It is to be emphasized that the diagram of FIG. 6 is functional, and as such, the blocks or boxes represented in the figure depict various functions that may be performed within the circuitry of the measuring device 38 so that it can perform its intended function of measuring the amount of radiation emitted from the scintillator 30'. The actual electronic circuitry within such functional boxes may take many and varied forms, as known to those skilled in the electronic arts. Such circuit details do not form part of the present invention.

The circuitry included within the measuring device 38 is also referred to as a skin dose monitor (SDM) circuit. The SDM circuit is typically contained on a single printed circuit board which is housed with four AA sized batteries is a plastic case. The ON/OFF switch 44 interfaces with a power ON/OFF circuit 60 which includes an electronic latch that switches a power transistor ON or OFF, which connects or disconnects the battery voltage, +V, to the measuring and processing circuits (i.e., the remaining circuitry of the SDM circuit), with the exception of the LCD display 46. Power is permanently connected to the LCD display 46 (so that it will always display—and thus record—the last radiation measurement made), which requires only a few microamps to function.

In a preferred embodiment, the power ON/OFF circuit 60 includes means for monitoring the battery voltage. The power source is four AA batteries, or 6 vdc. Should the supply voltage fall below 4.5 volts, a low battery condition is signaled by flashing the BATT. LED 45. Thus, whenever the battery LED 45 flashes, that is a signal that the batteries need replacing.

Light or photons received through the core 28 of the optical fiber 12, represented in FIG. 6 by the wavy arrows 62, is/are directed to a PIN silicon photo diode 64. Such diode 64 preferably exhibits an extremely low leakage current and works in a zero bias mode. Photo current flows through the diode 64 in proportion to the intensity or magnitude of the scintillation light that strikes the diode 64, which light in turn is a function of the radiation that is absorbed by the scintillator 30'. Such photo current is directed to a precision electrometer, which is nothing more than a resettable integrator 66. The output of the integrator 66 is constantly compared with a reference level $V_T$ by a comparator circuit 68. The reference level is adjustable by turning a selected calibration control (not shown). When the integrator output reaches the set reference $V_T$, a pulse generator circuit 70 (or equivalent) generates a pulse that increments an LCD Counter/Driver circuit 72. The pulse generator 70 then generates a reset pulse which is directed, over signal line 74, back to the integrator 66 to reset the integrator. (In some embodiments, a single pulse may be used to both increment the counter 72 and reset the integrator 66, e.g., with a leading edge of the pulse causing the counter 72 to be incremented, and a trailing edge of the same pulse causing the integrator 66 to be reset.) Once the integrator is reset, the measurement process repeats, with the integrator integrating up to the threshold $V_T$, the counter 72 incrementing, and the integrator resetting, for each measurement cycle. The more intense the light 62, the larger the photo current from the diode 64, and the more rapid the measurement cycle completes.

Pressing the reset button 48, which is coupled to a reset circuit 76 (which reset circuit may be as simple as a pull-up or pull-down resistor) resets both the integrator 66 and the LCD display 46.

A zero level clamp is applied to the integrator to prevent charge from accumulating within the integrator between measurements, thereby eliminating low level drift between measurements.

Advantageously, the entire SDM circuit uses only about 5 mA of current, which means that a set of four AA batteries will typically last between four and six months at a typical patient work load.

Although not shown in the drawings, it is noted that a suitable test box may be used with the invention as a means of checking out the operation of the SDM circuit 38 without the need for radiation. Such a test box has a short optical fiber cable with a suitable plug adapted to be plugged into the connector 40 (FIG. 2) of the SDM device 38. The test box includes a 9 volt battery, a timer circuit, a source of radiation, e.g., an LED, and a test button. When the test button is pressed, the timer starts which holds the power supply (battery) on for about ten seconds. A second timer switches on two seconds after the supply has been applied and connects current from a stablizied current source to the LED, which is optically coupled to the short length of optical fiber. The timer duration and current level are adjustable with externally accessible controls. These are factory set to give a reading of 100.0 mGy on a calibrated SDM, but can be readjusted to correspond to a user instrument calibration.

It is noted that the SDM circuit 38 may be adjusted (e.g., by adjusting the threshold voltage $V_T$) to provide a measurement of radiation using any suitable units. Radiation is typically measured in units of Rads or Grays (where 1 Gray=100 Rads). The dose rate measurement range of the SDM circuit may be as low as 1 milligray (mGy) per minute or as high as 3 Gray per minute. In order to facilitate display of the selected units, a removable front panel may be provided with the measuring device 38 so that the appropriate units for the display of the radiation is clearly marked.

It is thus seen that the present invention allows a physician or other medical technician to accurately monitor the dose being received by a patient in real time during an X-ray (or other imaging) procedure. Additionally, the total accumulated dose received by the patient during a given procedure is readily made available.

While the invention herein disclosed has been described by means of specific embodiments and applications thereof, numerous modifications and variations could be made thereto by those skilled in the art without departing from the scope of the invention set forth in the claims.

What is claimed is:

1. Radiation measuring apparatus comprising a sensor assembly including a sensor shrouded within a pad assembly that is transparent to the radiation to be measured and which facilitates mounting of the pad assembly on a surface, the pad assembly being disc-shaped and having a diameter less than about 50 mm, the sensor having a scintillating body which absorbs the radiation and converts it to light and means for measuring the intensity of the light emitted by the body and thereby indicating the amount of radiation to which the body had been exposed.

2. The apparatus according to claim 1 wherein the sensor assembly is detachably connected to the measuring means.

3. The apparatus according to claim 2 wherein the sensor assembly includes a flexible optical fiber by which light emitted by the scintillating body is conducted to the measuring means.

4. The apparatus according to claim 3 wherein one end of the flexible optical fiber has connector means attached thereto by which the flexible optical fiber is detachably connected to the measuring means.

5. The apparatus according to claim 3 wherein the scintillating body is shrouded by a reflective material which reflects light and tends to direct light emitted by the scintillating body impinging on the reflective material towards the optical fiber for transmission to the measuring means.

6. The apparatus according to claim 1 wherein the scintillating body and adjacent portions of the sensor assembly are shrouded by an opaque cover to prevent light other than that emitted by the scintillating body from reaching the optical fiber.

7. The apparatus according to claim 1 wherein the pad assembly is adapted to be secured to a surface by adhesive.

8. The apparatus according to claim 1 wherein the pad assembly comprises a flexible resilient material.

9. The apparatus according to claim 1 wherein the measuring means includes resettable means for measuring and displaying total amount of radiation to which the scintillating body of the sensor assembly has been exposed.

10. The apparatus according to claim 1 wherein the measuring means includes rate means for measuring and displaying the rate of radiation exposure to which the scintillating body of the sensor assembly has been exposed.

11. The apparatus according to claim 1 wherein the scintillating body comprises a thallium doped caesium iodide crystalline material.

12. The apparatus according to claim 1 wherein the scintillating body comprises zinc cadmium sulphate-Ag.

13. The apparatus according to claim 12 wherein the scintillating body is made from powdered particles reconstituted into a thin flat scintillating disc.

14. The apparatus according to claim 1 wherein the scintillating body is less than 0.3 mm thick.

15. The apparatus according to claim 14 wherein the scintillating body comprises a disc that is no greater than about 1 mm in diameter and no thicker than about 0.25 mm.

16. The apparatus according to claim 1 wherein the scintillating body has a volume that is less than 0.3 cubic mm.

17. Radiation measuring apparatus comprising:
a sensor assembly including a sensor having a scintillating body made from Zinc Cadmium Sulphate-Ag powdered particles reconstituted into a thin flat scintillating disc which absorbs radiation and converts it to light, the thin flat scintillating disc being mounted on a base disc;
a flexible optical fiber overlaying a portion of the base disc so that a first end of the flexible optical fiber is positioned adjacent the thin flat scintillating disc, and wherein a mirrored surface, positioned at an angle relative to the base disc, overlays the thin flat scintillating disc so as to direct light emitted by the thin flat scintillating disc into the flexible optical fiber, and further wherein an opaque molding layer shrouds the thin flat scintillating disc, angled mirrored surface, and the first end of the flexible optical fiber; and
means for measuring the intensity of the light emitted by the thin flat scintillating disc and thereby indicating the amount of radiation to which the thin flat scintillating disc has been exposed.

18. The apparatus according to claim 17 wherein the mirrored surface is positioned at an angle of approximately 45 degrees relative to the base disc.

19. The apparatus according to claim 17 wherein the base disc includes a fold wherein a portion of the base disc is folded up, said folded up portion of the base disc having a hole therein through which the flexible optical fiber passes, said folded up portion thereby providing a strain relief for the optical fiber.

20. A sensor assembly suitable for sensing radiation comprising:

a flexible optical fiber having proximal and distal ends, a plug connector at the proximal end;

a sensor at the distal end, the sensor comprising:

a scintillating body made from powdered particles reconstituted into a thin flat scintillating disc positioned adjacent the distal end formed of a material which emits light when the scintillating disc is exposed to radiation;

a base disc on which the thin flat scintillating disc is mounted, the base disc facilitating attachment of the thin flat scintillating disc to a surface, and wherein the flexible optical fiber overlays a portion of the base disc so that the distal end of the flexible optical fiber is positioned adjacent the thin flat scintillating disc;

a mirrored surface positioned at an angle relative to the base disc so as to direct light emitted by the thin flat scintillating disc into the flexible optical fiber, and a molding layer that shrouds the thin flat scintillating disc, angled mirrored surface, and the distal end of the flexible optical fiber, the molding layer being transparent to X-ray radiation, but being opaque to light emitted from the thin flat scintillating disc.

21. The sensor assembly of claim 20 wherein the mirrored surface is positioned at an angle of approximately 45 degrees relative to the base disc.

* * * * *